United States Patent [19]

Baker, Jr. et al.

[11] Patent Number: 5,237,991
[45] Date of Patent: Aug. 24, 1993

[54] IMPLANTABLE MEDICAL DEVICE WITH DUMMY LOAD FOR PRE-IMPLANT TESTING IN STERILE PACKAGE AND FACILITATING ELECTRICAL LEAD CONNECTION

[75] Inventors: Ross G. Baker, Jr.; Reese S. Terry, Jr., both of Houston, Tex.

[73] Assignee: Cyberonics, Inc., Webster, Tex.

[21] Appl. No.: 794,990

[22] Filed: Nov. 19, 1991

[51] Int. Cl.⁵ .............................................. A61N 1/37
[52] U.S. Cl. ..................................................... 607/27
[58] Field of Search ...................... 128/419 PT, 419 P

[56] References Cited

U.S. PATENT DOCUMENTS

| | | | |
|---|---|---|---|
| 3,508,538 | 4/1970 | Keller, Jr. ...................... | 128/419 PT |
| 3,625,201 | 12/1971 | Murphy, Jr. .................. | 128/419 PT |
| 3,800,801 | 4/1974 | Gaillard ........................ | 128/419 PT |
| 4,347,849 | 9/1982 | Congdon ........................ | 128/419 P |
| 4,423,732 | 1/1984 | Tarjan et al. .................... | 128/419 P |
| 4,476,869 | 10/1984 | Bihn .............................. | 128/419 PT |
| 4,556,061 | 12/1985 | Barreras et al. ............. | 128/419 PT |
| 4,585,004 | 4/1986 | Brownlee ...................... | 128/419 PT |
| 4,605,007 | 8/1986 | Heraly .......................... | 128/419 PT |
| 4,705,042 | 11/1987 | Giurtino ........................ | 128/419 PT |
| 4,830,005 | 5/1989 | Woskow ........................ | 128/419 PT |
| 4,979,506 | 12/1990 | Silvian .......................... | 128/419 PT |
| 5,003,975 | 4/1991 | Hafelfinger et al. .......... | 128/419 PT |

OTHER PUBLICATIONS

Center et al, "Journal of Thoracic & Cardiovascular Surgery", V. 61, No. 5, May 1971, pp. 752-754.

*Primary Examiner*—William E. Kamm
*Attorney, Agent, or Firm*—O'Connor, Cavanagh, Anderson, Westover, Killingsworth & Beshears

[57] ABSTRACT

An implantable medical device is provided with a removable dummy load across its connector output terminals to allow the device to be tested without removal from the sterile disposable package in which it is shipped and stored. The dummy load is confined with the device entirely within the sterile package to simulate the electrical impedance across the output terminals when the device is implanted in a patient and connected to an electrical lead for tissue stimulation. Testing is performed using a conventional external programmer normally provided for programming and monitoring output functions and parameters of the device. The programmer communicates by telemetry with the device confined within the package, to test selected functions and parameters. The dummy load has posts adapted to mate with the receptacles of the electrical connector of the device, and to be secured mechanically and electrically in the receptacles by set screws. The posts are dimensioned to provide a mechanical stop for the set screws when tightened down, and, when the set screws are backed off slightly from the posts to allow removal of the dummy load, to permit the proximal terminals of the replacing lead to be fully inserted into the receptacles without obstruction by the set screws.

5 Claims, 1 Drawing Sheet

IMPLANTABLE MEDICAL DEVICE WITH DUMMY LOAD FOR PRE-IMPLANT TESTING IN STERILE PACKAGE AND FACILITATING ELECTRICAL LEAD CONNECTION

BACKGROUND OF THE INVENTION

The present invention relates generally to implantable medical devices, and more particularly to implantable devices, such as tissue stimulators, which are adapted to be tested within the sterile package in which they are encapsulated at the time of manufacture.

Implantable medical devices of the type with which the present invention is concerned are adapted to deliver a predetermined therapeutic regimen to treat and/or control a disorder which may be of medical, psychiatric, neurological or other origin. They may operate manually or automatically, in response to an external activation signal (e.g, a magnet applied by the patient, movement of the patient, etc.) or to a signal developed in response to an internally generated parameter, action or sensation of the body (e.g., respiration, a chemical change, etc.) or of the implanted device itself (e.g., a timing signal, jarring action, etc.). Typically, such devices are programmable so that they may be adapted to provide the specific treatment required by the nature of the disorder of a particular patient, being provided with ranges of operating parameters, functions, features and characteristics suitable for treatment of many variations within a class of disorder. Examples are nerve stimulators and cardiac pacemakers, but the principles of the invention are not limited to those devices.

With programmable devices, specific initial settings of certain functions of the device appropriate to an individual patient may be selected within the broad operating ranges applicable to all patients who may require the therapy provided by the device. After implantation, the initial settings may be modified within those ranges and the device operation monitored, through telemetry, from outside the patient's body by use an external programming unit, or programmer, which is designed for the particular class of device. Different device manufacturers usually develop and market their own programmers which are specially designed for use with their devices, but all such programmers have many common or substantially similar features and capabilities, including that of communication with the implanted device by a telemetry system which utilizes components in both the programmer and the implanted device to transmit and receive commands and replies. Use of the programmer, of course, is limited to physicians and other medical care providers who are authorized and licensed by the appropriate authorities such as state medical boards to diagnose illnesses and disorders and to administer treatment to patients.

A requirement common to all implantable medical devices is that the device must be in a sterile condition at the time it is implanted into the patient's body. After the device is manufactured and tested, it is sterilized and encapsulated in a sterile package, where it remains throughout shipment, storage and the like, until it is removed for the implantation. Additional protection may be used in the form of an outer package such as a blister pack in which the inner sterile package is confined. Prior to implant, the device is tested again to assure that it is still fully operational and has a sufficient level of energy remaining in its battery.

It is a principal object of the present invention to provide improved apparatus and methods for enabling implantable medical devices to be tested prior to implant. The principles of the invention are applicable to any implantable medical device which utilizes telemetry for programming and/or monitoring the device operation.

Currently, techniques used for testing implantable medical devices require that the device be removed from the package. Artificial cardiac pacemakers, for example, are tested just before being implanted, using a relatively complex pacing system analyzer. In the test procedure, a cable which has been sterilized is plugged at one end into the analyzer and hooked at the other end to leads of the device. Tests are then performed to verify that the threshold of the leads is acceptable. That cable is then removed and a different cable, which must also be sterilized, is plugged into the pacemaker pulse generator to measure its capability to sense and pace properly. Such analyzers are expensive, present reliability and other problems, require that cables used in the testing procedure be sterile, and present another piece of equipment with which the surgeon or a biomedical engineer, technician or technical representative standing by to assist must be thoroughly familiar with and use at the time of implant.

Such testing is performed with the implantable medical device positioned in the sterile field, so that further sterilization of the device itself is not required. The signal (e.g., pulse) generator or other apparatus constituting the device is necessarily removed from the disposable package in which it was shipped and stored, and the patient is waiting with an open incision, in preparation for the implant. Testing of the device at this point delays the entire operating room procedure. Moreover, although rare, if t he tests reveal a device which is either defective or has an overly depleted energy source, a new device must be obtained from inventory, if available, and tested, further delaying completion of the surgical implantation procedure.

Some time ago, it had been proposed to package an implantable pacemaker pulse generator with a flex circuit as part of the packaging. The leads of the generator were connected to the flex circuit, and the connections exited the package so that it was possible to plug the generator from outside the package into an external pacing system analyzer. The pulse generator could then be tested within the package using the external analyzer.

Another prior art test setup involved the use of wires connected to the outputs of a defibrillator pulse generator, running to connectors on an inner sterile blister package and then other wires running from those connectors to an outer blister package. This provided two levels of connectors for electrical access to the packaged defibrillator from the outside world, and allowed a lead/electrode system implanted in the patient to be connected to the pulse generator for use in testing the lead while the generator remained in its sterile package. Alternatively, an external resistor could be plugged into the generator, across the defibrillating terminals, to verify that a defibrillating shock could be delivered by the generator across the resistor.

The use of connectors or other means on the package for access to the medical device inside the package adds significantly to the problem of maintaining a sterile environment within the package. Also, only very limited monitoring and testing can be performed using such prior art arrangements, with an added requirement that the implanting physician be thoroughly familiar with a specialized test procedure. At least partially testing the device while it is in its package, however, reduces the number of tests and associated delays during the implant procedure. The capability of reliable and relatively thorough testing of the implantable device within its sterile unbroken package would allow the entire test procedure to be performed and identification and replacement of a defective or energy-depleted device before the operating room procedure actually begins. Elimination of testing as part of the surgical procedure itself would permit that procedure to be performed more efficiently and smoothly than is now the case.

Therefore, another important object of the invention is to avoid implantation of a defective or energy-depleted medical device by adapting the device intended for implant to be substantially fully testable within its sterile unbroken package so that final testing of the device may be performed just before, rather than after, it is removed from its package for implantation. Although such capability would also allow testing of the device after it is received at the hospital and before it is placed in inventory, it is more prudent to conduct the tests on the day the surgical procedure is to be performed. This guards against the possibility that abuse has occurred, a random defect has erupted, or the battery has become depleted while the packaged device was in hospital or other medical facility inventory.

SUMMARY OF THE INVENTION

The present invention provides improved apparatus and methods for relatively thorough testing of an implantable programmable medical device before it is removed from its sterile packaging. Accordingly, the manufacturer may test the packaged device to verify proper operation at the time it is withdrawn from inventory for shipment to a hospital to be made available for implant. The packaged device can also be tested when at the hospital just before implantation, without removal from the package.

The testing is performed using only the conventional programmer intended by the manufacturer to be employed for programming the device parameters to the needs of the patient receiving the implant. Costly, complex test equipment traditionally used to test devices before implantation is not required, nor persons trained in the use of such traditional equipment. External connections, which might adversely affect sterility, are not required, and the tests may be performed without violating device sterility.

According to the invention, a dummy load such as a discrete resistor or other passive or active impedance device is releasably connected to an electrical connector at the output of the implantable device. The dummy load is contained entirely within the sterile package with the device. The load simulates the approximate electrical impedance at the output terminals when the device implanted in the patient. The most critical operating functions of the device may be tested as though it were implanted, before removal of the device from the package. This capability is facilitated by the current drain through the load and the current flow in other portions of the circuit path of the device. Output parameters are automatically varied across the dummy load resistor. The device need not be limited to a single resistor, but may have a plurality of points of access to its circuitry and separate dummy load means connected to each of them.

The device communicates by telemetry with the conventional external programmer employed to program and monitor its functions and parameters. Unlike conventional telemetering, however, the programmer is used to activate and communicate with the device for test purposes before it is removed from its sterile package. Every experienced implanting physician is familiar and comfortable with the conventional programmer, and it is the only piece of "test" equipment required to verify that the device is operational.

The device includes a primary voltage source such as a battery, and may also include a separate reference voltage source to detect parameter value drift during testing. In an implantable stimulator, for example, an internal voltage reference establishes voltage levels required to produce desired output voltages and currents. The same reference may be used to establish a regulating target for supply voltages for the internal electronics and for monitoring the battery condition. The same voltage source may be used as a reference for the telemetry system that monitors the device outputs, and in generating test inputs to a sensing system. On the other hand, a single source might be preferred to avoid added complexity and current drain. Also, a second, independent source might, if not of different design or located on a different integrated circuit, lack independence and display the same errors as the primary voltage source.

Nevertheless, an independent voltage source is preferable to circumvent potential long-term drift of a primary source attributable to imposed stresses or latent manufacturing defects. The system itself is unable to detect such drift. If the voltage were to discuss by 25 percent, for example, all programmed output currents and output voltages of the device would decrease by a corresponding percentage. But telemetry measurements of these parameters would not reflect the change because they are referenced to the smaller voltage level. Similarly, if the sensing system had test inputs reduced by 25 percent, it would go undetected because the threshold targets would be similarly reduced. Therefore, system generation of test inputs and measurement of outputs using a second reference is desirable.

It is possible to use the battery voltage itself as a voltage reference for verification of the primary reference, such as where the battery displays highly predictable voltages under light impedance loads.

A secondary time base may be used for similar reasons, and to limit the frequency of output pulses of a stimulator, for example, for device safety unrelated to device testing. However, the external programmer is capable of verifying the accuracy of the primary time base by timing the interval between telemetry markers transmitted by the implantable device in synchronism with the delivery of output pulses.

The invention also provides a solution to the problem of connecting the implanted pulse generator to an implantable lead for tissue stimulation or signal sensing. Many implantable devices have an electrical connector on the device housing in which female receptacles accept and mate mechanically and electrically with male terminals of the lead. Tiny set screws in the connector are then tightened down on the male terminals to secure them within the female receptacles.

In practice, the set screws may not be sufficiently threaded into their tapped holes, which could allow them to be dislodged in shipping and handling of the packaged device. Although still in the package, the dislodged set screw(s) may be difficult to locate under the pressures of the surgery, so that the sterile package of another such device must be broken to retrieve sufficient set screws for the task.

On the other hand, the set screws may be screwed down too far when the device is being packaged, and thus prevent full insertion of the lead terminals into the receptacles when the device is implanted. The implanting physician may be unaware that the set screws are actually blocking the path, because the terminals may be frictionally engaged with the receptacles enough to appear that they are fully inserted. When the set screws are tightened down they will not engage the terminals. Unless the physician tugs sharply on each terminal, the lack of secure engagement may remain unnoticed if there is sufficient electrical contact to obtain readings and results. Discovery that the implanted system is not operating properly may not be made until the terminals have been dislodged from electrical contact with the receptacles a few days or so after the implantation procedure.

The male terminals of the dummy load resistor are made at least as thick (e.g., in diameter) as the male terminals of the implantable lead. When the resistor is removed from the device after testing, the set screws, which had been tightened down on the resistor terminals rendering them incapable of being dislodged even in rough handling, are backed out slightly to allow retraction of the resistor terminals from the receptacles. The lead terminals are then readily inserted fully into the same receptacles, being not greater than the size of the resistor terminals, without abutting against the set screws. When the set screws are then tightened they will engage the lead terminals to retain them in the receptacles.

A separate circuit in the device measures selected electrical parameters, such as the magnitude of the delivered output pulses, and tests selected operating functions of the device in its package after the device is activated by the external programmer. The system may also be used for testing the sense amplifier and other components in the input circuit of the device adapted to detect a parameter internal or external to the patient's body to trigger or vary the therapy delivered by the device, by means of an internal signal generator controlled from the external programmer.

BRIEF DESCRIPTION OF THE DRAWINGS

The above and still further objects, features and attendant advantages of the invention will become apparent from a consideration of the following detailed description of certain preferred embodiments thereof, taken in conjunction with the accompanying drawings, in which.

DETAILED DESCRIPTION OF THE PREFERRED EMBODIMENTS

Figure 1:
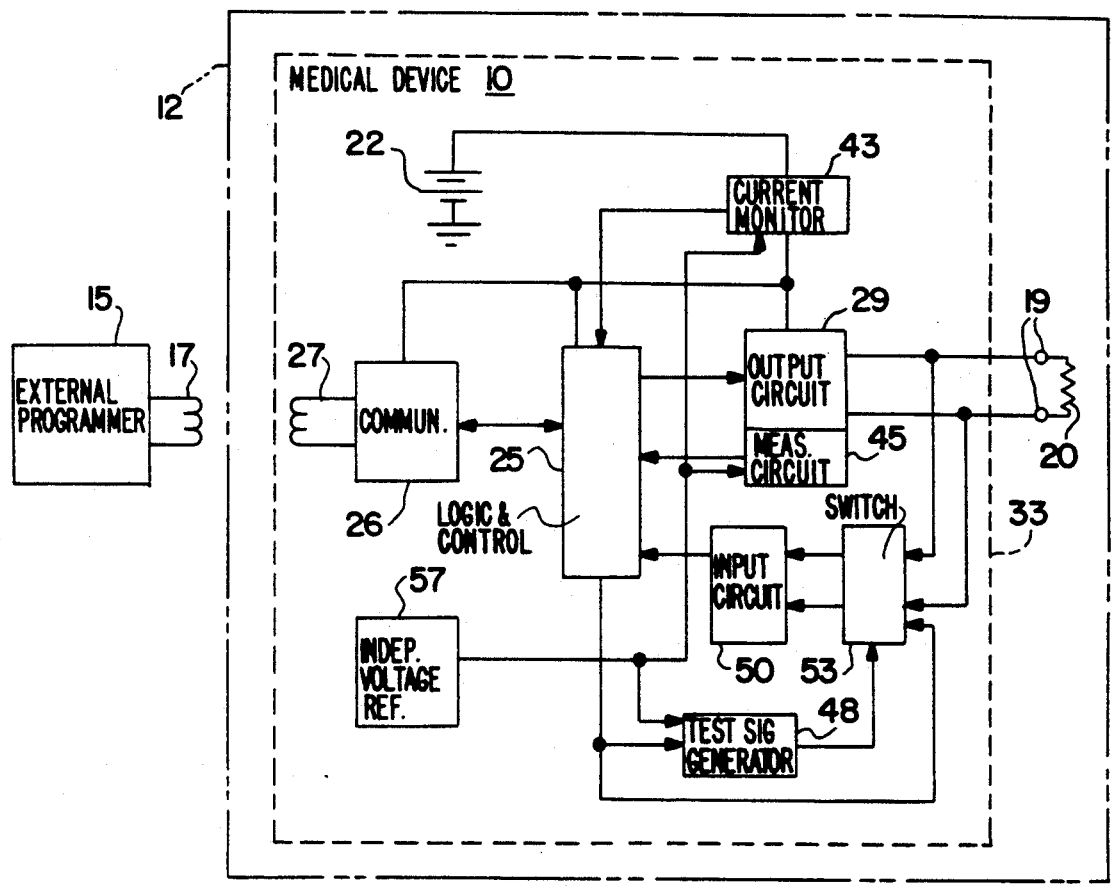
FIG. 1 is a simplified block diagram of the electrical circuitry of an implantable medical device and an associated external programmer, useful for describing a preferred embodiment of the invention.

FIG. 1 is a block diagram of an implantable programmable medical device 10 such as the stimulus or pulse generator of an electrical nerve stimulator of a type manufactured by Cyberonics, Inc. of Webster, Tex. ("Cyberonics") for use in the treatment and control of epilepsy. The device of FIG. 1 has been modified according to the invention to allow it to be tested while it is confined entirely within its unbroken sterile package 12. For reasons stated above, it will be understood that the invention is not limited to this or any other specific implantable programmable medical device. An external programmer 15 is provided for use by the surgeon (and by the patient's attending physician) to program device 10 according to the needs of the particular patient, and for monitoring the functions and electrical parameters of the device during its operation. The programmer 15 is conventional in every respect, in the sense that it is not modified in any way for use in the system of the present invention from its structure and operation for use in normal programming and monitoring of the implanted device.

The programmer may include a PC (personal computer or the like, including monitor) console, desktop, portable or notebook size, with software and keyboard or control panel implemented to provide the various command and related functions necessary to perform its normal programming and monitoring functions with respect to the implanted device. Typically, the programmer includes a wand (not shown) connected to the PC for placement in proximity to the implanted device to facilitate programming and monitoring. In the illustration of FIG. 1, programmer 15 is simply shown as having an antenna 17 by which it communicates through telemetry with device 10.

In the case of Cyberonics implantable neurostimulator device Model 100, the related external programmer is an IBM or IBM-compatible PC with Cyberonics wand Model 200 and software package 250. As was noted earlier herein, each manufacturer of implantable programmable medical devices generally designs, develops, manufactures and/or markets one or more external programmers for use with a particular type or family of its implantable devices, and such programmer(s) would be usable in conjunction with the teachings of the present invention for testing that device or device family.

For the sake of simplicity, the neurostimulator constituting the exemplary implantable medical device 10 with which the apparatus of the present invention may be used is shown with only its major functional blocks in FIG. 1. A more detailed description of a basic neurostimulator is disclosed in copending U.S. patent application Ser. No. 07/434,985, filed Nov. 10, 1989, now U.S. Pat. No. 5,154,172 in the names of Reese S. Terry, Jr., et al. assigned to the same assignee as the instant application, and incorporated herein by reference. However, the illustration of FIG. 1 herein will suffice for purposes of an understanding of the invention.

The overall neurostimulator would include implantable stimulating electrodes and a lead system for applying the output signal of the medical device (stimulus generator) 10 to a selected nerve of the patient, by connection of the lead to output terminals 19 of the generator. In FIG. 1, however, an electrical resistance 20 is shown connected to terminals 19, about which more will be said presently. Generator 10 includes a battery 22 of a type conventionally employed in implantable medical electronic devices, such as a single lithium thionyl chloride cell. In this example, the battery supplies power to the entire generator including a microprocessor-based logic and control section 25, which, among other things, controls the programmable functions of the device 10. The programmable functions may include parameters such as, for example, output current or voltage, output signal frequency, output signal pulse width, output signal on-time, output signal off-time, daily treatment time for continuous or periodic stimulation, and output signal start delay time.

Programmability of this and other types of implantable medical devices allows the output signal to be selectively tailored to the needs of the individual patient for treatment and control of a specific disorder. Timing signal and telemetry communications with external programmer 15 for the logic and control functions of the generator are provided by a communications circuit 26 with associated antenna 27. Once the system is programmed, it operates continuously at the programmed settings until they are reprogrammed (by the attending physician) using the external programmer. Operating parameters of the device dictated by the programming are displayed on a monitor of the programmer, either directly by virtue of the programming or from telemetry signals transmitted by the device.

Logic and control section 25 controls an output circuit 29 which generates an output signal having parameter values determined by the programming, for treatment of the disorder of interest in the implant patient. The programmed output signal appears at output terminals 19 for delivery to tissue-stimulating electrodes at the distal end of an implantable lead (not shown) connected to the output terminals when the overall device is implanted. A typical implant location for a medical device such as stimulus generator 10 or a pacemaker pulse generator is within a pocket formed by an incision just below the skin in the patient's chest. Electrical terminals at the proximal end of the implanted lead would be connected to output terminals 19 at an electrical connector on the housing of device 10 and the stimulating electrodes at the distal end of the lead properly positioned and secured in electrically activating relation to the tissue to be stimulated.

Figure 2:
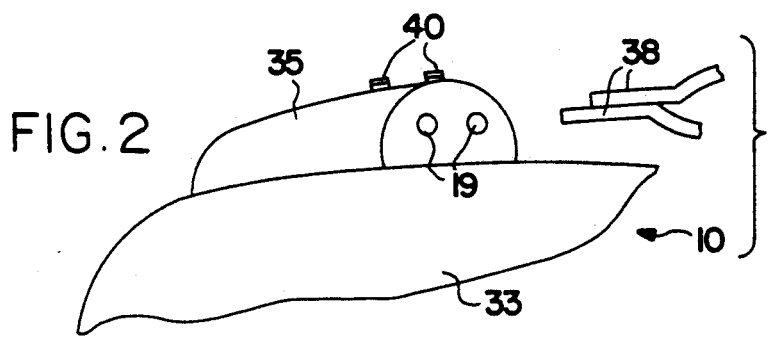
FIG. 2 is a fragmentary perspective view of a portion of an implantable medical device housing with electrical connectors useful in describing a mechanical aspect of the invention.

According to the invention, resistance 20 is releasably connected across the output terminals of the implantable medical device 10 upon completion of device manufacture, and, with the device, is sterilized and encapsulated in the sterile package 12. The value of resistance 20 is selected to approximate the electrical load impedance which would be presented to the device, such as by the lead, electrodes and patient tissue and fluid therebetween in the example of a neurostimulator, when the device is actually implanted. In the exemplary embodiment of such a device, the value of resistance 20 is two kilohms. In practice, the components and circuitry of medical device 10 are encased in a housing 33 represented by the dashed line in FIG. 1 and shown in fragmentary perspective view in FIG. 2.

An electrical connector 35 on the housing 33 (FIG. 2) has a pair of female connectors or receptacles 19 which are electrically connected to the output circuit 29 of the device. Mating male terminals 38 on the resistor 20 are plugged into receptacles 19 to make electrical contact with them, and after being fully inserted are securely engaged mechanically and electrically by tightening down set screws 40 on the connector 35. This is a releasable connection in the sense that the resistor may be readily removed from the device 10 by simply partially unscrewing the set screws sufficiently to allow the terminals of the resistor to be withdrawn from the receptacles in the connector.

In the usual situation in which a medical device is conventionally encapsulated in a sterile package, nothing would be inserted in receptacles 19. Set screws 40 would be conveniently threaded into their tapped holes above the receptacles for retention while the packaged device is in transit and ready availability at the time of implant. In such a situation, two possible undesirable scenarios may be encountered. One possibility is that the screws were not threaded sufficiently into their tapped holes to be retained during the travails of shipment and handling. Another possibility is that the screws are threaded in too deeply, which causes them to block the terminals of the lead from fully entering the receptacles. Either possibility may present a problem to the implanting surgeon.

According to another aspect of the invention, however, each of terminals 38 of resistance 20 is dimensioned to be just slightly thicker than (but at least as thick as) the thickness of corresponding terminals of the implantable lead to be used with the device. When the resistor's terminals are inserted into the receptacles of connector 35 and set screws 40 are tightened down, the terminals become tightly engaged in the receptacles. Under these conditions, there is no danger that the set screws are either too loose and likely to fall out in transit or handling of the package, or tightened too deeply into the receptacles. Because the terminals of the resistor are at least as thick as the terminals of the implantable lead ultimately to be inserted in connector 35, when the set screws are unthreaded sufficiently to allow the resistor to be removed from the connector the terminals of the lead will not be obstructed by the set screws and are fully insertable into the receptacles of the connector.

With the resistor plugged into the connector while the medical device is in its sterile package, the device may be fully tested using only the external programmer. The resistor acts as a dummy load and, when the device is activated by the programmer, assures current consumption substantially equivalent to that which would normally be encountered in the implanted device. Effectively, the programmer allows the device to be "put through its paces", including tests of programming and monitoring its operating parameters and functions, while it is still entirely confined within the sterile package. Using the same telemetry by which the device is conventionally programmed, monitored, and reprogrammed after implantation, various parameters such as output current delivered to the load, total current drain, pulse amplitude and duty cycle of the packaged device are readily measured and may be adjusted as necessary for proper operation.

The capability to monitor the current drain of an implantable device while it is in its sterile package, using telemetry, provides a very sensitive indication of the existence of any operational problems. Virtually any defect or failure in an implantable device affects current drain and can therefore be detected, even if not precisely pinpointed, in this very simple and effective manner. Even if a particular parameter cannot be measured directly, it can often be discerned indirectly through the measurement of current drain of the device. For example, programming an increase in output pulse amplitude will cause the current drain of the device to increase in a known way. Thus, by using telemetry through the external programmer and an implantable programmable device packaged with a dummy load, virtually the entire system to be implanted can be subjected to reasonably thorough testing. In addition, the system can be programmed to do a self-test on itself while in the sterile package.

Additional features include a current monitor 43, and a measurement circuit 45 associated with output circuit 29 of the device. Current monitor 43 measures the actual current consumption of the overall implantable device and of its various component circuits. In the latter respect, although connections to only some of the components are shown in FIG. 1, it will be understood that electrical connections exist between it and every other electronic circuit in the device for purposes of such measurements. The current monitor may be embodied in a small valued resistor in series circuit with the power source which has its differential voltage amplified, low pass filtered with a time constant of about three seconds, and converted to the digital domain by an analog to digital converter. The digital value is communicated to the external programmer 15 via telemetry through means of the logic and control circuit 25 and communication circuit 26 and the respective antennas.

In this way, the programmer determines current consumption of the overall implantable device and its component parts as a function of the programmed parameters of the device. Excessive or insufficient current consumption is detected by comparison with known limits by the programmer, and may be flagged as a device failure to the person doing the testing. Consequently, a defective device can be detected while still in its unbroken package and replaced with a satisfactory working device to be implanted in the patient, before the actual surgical procedure is commenced.

The measurement circuit 45 operates in connection with the output circuit 29 of device 10 to evaluate the magnitude of the delivered output pulses. Two implementations of such a system are disclosed in copending U.S. application Ser. No. 07/738,801 of Ross G. Baker, Jr., assigned to the same assignee as the instant application, and incorporated herein by reference. In one implementation, the current is sampled as a voltage across a resistor, amplified, and its value at a predetermined point in time (such as at the end of a pulse) is held and converted to a digital value. The analog to digital conversion is dependent on the accuracy of a voltage reference. In another implementation, the detected current is integrated to produce an output proportional to the charge delivered, rather than the current delivered, in the output pulse.

Thus, the device incorporates telemetry and circuitry which allow measurement of the device parameters to verify that they are varying in a predictable manner as the device's inputs and outputs are varied, as would be the case for a properly functioning device. The incorporated circuits also allow estimation of the total current drain of the device.

For a device with sensing inputs, the invention also permits the injection of synthetic input signals in a self-test mode. That is, if the implantable device has input circuitry (for example, to receive signals from selectively positioned sensors, which will affect its output), additional circuitry may be utilized within the device itself to exercise this input circuitry in the self-test mode. In the preferred embodiment of the invention, such capability is provided by a test signal generator 48 having an output which is conveniently switched into the input circuit 50 of the device by means of a switch 53. The test signal generator need not be sophisticated, and in fact may be very crude.

The input circuit receives the test signal, such as a pulse or train of pulses of predetermined amplitude and rate, to test, for example, the sense amplifier circuitry of the device. This is accomplished by having the external programmer switch the input to be supplied to input circuit 50 from the input lead connected to the "outside world" (e.g., for a sense signal) to the output of test signal generator 48. The test signal generator may produce an input test signal of constsnt amplitude, and the sensitivity of the sense amplifier is then adjusted until this input test signal is sensed. If the level at which that sensing takes place corresponds to or is less than the amplitude of the actual signal expected to be delivered to the input circuit, the device has passed that test. If the test signal is provided with multiple different amplitudes, the test reliability is improved.

For many of the intended purposes of the invention, the load resistor 20 might, like the test signal generator 48, be arranged and adapted to be switched in and out. That is, a switch could be interposed between the output circuit and the resistor to allow selective connection and disconnection of the dummy load, instead of having the resistor plugged into the connector 35 at the output of the device. However, the latter arrangement is preferred because the use of a simple releasable connecting means allows the surgeon to mechanically disconnect the load resistor quickly and easily when the device is removed from its package, for replacement with the associated lead (or other delivery means). Also, if a switch were used in place of the electrical connector to connect the resistor 20 to the device output for purposes of testing, the mechanical and electrical performance of connector 35 itself would not be tested at the same time. It might then be necessary to perform a separate check of the connector's reliability.

The programmer correlates the measured telemetry values with stored information representing values of properly functioning units. If the device fails the tests or is suspect in any way, it may be rejected at either of at least two points where the in-package testing is likely to be performed. The first of these is just prior to shipment of the packaged device to the hospital, physician's office or other location where it will be held in inventory pending the need for an implant. The second point is just prior to implantation of the device. Testing is readily performed at either or both of these points, or at any other time prior to implant, to assure that a properly functioning device is being implanted in the patient.

With the resistor 20 connected to the terminals 19 of output circuit 29 of the packaged device, the external programmer 15 may be used to command the device to produce its normal quiescent current with no output pulses being generated. The output circuit may then be reprogrammed to generate increasingly higher output pulse amplitudes to obtain a reading of the current consumed by the entire device. The current and/or voltage delivered by the output circuit can be measured by measurement system 45 in output circuit 29, over a full range of output pulse amplitudes. These measurements may be repeated as the pulse width is varied, to obtain an indication of the device operation over a range of pulse parameters, by which to determine whether the device is operating within specifications. For example, change in current consumption would be expected as output pulse amplitude is varied.

If appropriate markers are transmitted by telemetry from the packaged device in synchronism with the output pulses generated by the device, the pulse frequency may be detected externally from the telemetry signal. The output frequency may be varied for a given pulse amplitude and pulse width, and the current drain of the device may then be measured using current monitor 43. As the pulse frequency is increased, device current consumption should increase. All of these tests and measurements may be programmed in the device with the external programmer, along with an indication of allowable values and ranges of values for the measured parameters. Device operation may be varied over a representative sample of the device parameters to verify that current drain is appropriate for the value of the particular load resistor.

In testing just prior to an implant, the external programmer may itself be suitably programmed to run a complete test of the device. In such a case, the physician need only turn on the programmer, and, when the menu is presented, merely select the appropriately labeled test program, such as "pre-implant test". The programmer would be adapted for that selection to proceed through an entire testing program automatically, and, when completed, to inform the physician by means of its display monitor that the device is good (if that conforms to the test results) and to proceed with the implant.

The system of the invention could be adversely affected if independent measurement standards were lacking. To alleviate the possibility of drift, a second voltage source used for comparison against the first voltage source would assure minimal parameter shift. Referring again to FIG. 1, device 10 has battery 22 as a voltage source and, in the preferred embodiment, also includes an independent reference voltage source 57 for detecting drift of parameter values during testing of the device. The independent voltage source supplies a reference voltage to overcome potential long-term drift of the primary source which may be caused by imposed stresses or latent manufacturing defects, and an inability of the system to detect such drift in the absence of an independent reference voltage. The system generates test inputs and measures delivered outputs from the reference. An alternative arrangement is to provide first and second voltage reference sources whose levels are measured and compared. The difference, if any, between the measured values of the two references is supplied to logic and control circuit 25 and the reference from the first source is delivered throughout the device.

The battery voltage itself may be used as a voltage reference for verification of the primary reference, such as where the battery exhibits highly predictable voltages under light internal impedance loads. The battery may be periodically placed under controlled light load conditions to verify the internal reference against the terminal voltage of the battery.

The time base provided by an oscillator may also create problems, because a known frequency must be employed. A second time base may be used in the device for reasons similar to those mentioned above for use of a second voltage reference. Instead, the frequency source of the external programmer may be used to verify the accuracy of the time base externally by causing the implantable device to transmit a telemetry marker which is synchronous with the delivery of output pulses, and to time the inter-marker interval at the programmer. Further assurance is obtained by virtue of the fact that as the pulse width is varied the device current consumption changes in a known manner with time. With these safeguards, any significant discrepancy in the time base would be readily observed.

Although a presently preferred embodiment and method have been described herein, it will be apparent to those skilled in the field of the invention from a consideration of the foregoing description, that variations and modifications of the disclosed embodiment and method may be made without departing from the spirit and scope of the invention. It is therefore intended that the invention shall be limited only to the extent required by the appended claims and the rules and principles of applicable law.

What is claimed is:

1. A sterile packaged implantable programmable medical device having operating functions for electrically stimulating selected excitable tissue in a patient's body when the device is implanted after removal from its sterile package, comprising:

a medical device adapted to be implanted in a patient;

package means for encapsulating the device in a sterile environment for transport and storage in preparation for implantation;

the device including:

electrical circuit means responsive to predetermined signals generated external to the package means for programming electrical output parameters of the device included within said operating functions, the electrical circuit means including:

battery means for powering the device, and telemetry means for sending and receiving telemetry signals including at least some of the externally generated predetermined signals to and from the device, whereby to enable communication between the device and a telemetry system external to the package means adapted to program and monitor electrical output parameters of the device, a case housing the electrical circuit means, and an electrical connector including output terminals connected to the electrical circuit means, adapted to deliver the electrical output parameters of the device to a load presented when the device is implanted in the patient and connected by the output terminals to proximal terminals of an electrical lead for electrical interaction with the tissue to be stimulated; and dummy load means contained entirely within the package means for simulating the approximate electrical impedance of said load, the dummy load means including load terminals connected to the output terminals of the connector;

the connector further including fastener means for securely fastening the load terminals of the dummy load means mechanically and electrically to the output terminals of the connector within the package means, and for disconnection therefrom after the device is removed from the package means and before implantation in the patient, whereby at least some of said operating functions of the device may be tested and test measurements monitored by means of the telemetry signals as though the device were implanted in the patient, before removal of the device from its sterile package, and the load terminals of the dummy load means providing a mechanical stop for the fastener means when the load terminals are securely fastened to the output terminals of the device, to assure reliable connection of the proximal terminals of the electrical lead to the output terminals when the dummy load means is replaced by the electrical lead.

2. The invention of claim 1, wherein the electrical circuit means further including reference means for detecting drift in the values of the output parameters over time when test measurements are monitored.

3. The invention of claim 1, wherein said electrical circuit means in combination with the dummy load means comprises means for detecting and communicating to the telemetry means, for external monitoring by the telemetry system, the current drain at preselected locations of the electrical circuit means in response to certain ones of the telemetry signals received by the telemetry means.

4. The invention of claim 1, wherein said electrical circuit means further includes:
   measuring means for monitoring at least some of the electrical output parameters of the device.

5. The invention of claim 1, wherein the output terminals of the connector comprise receptacles, the load terminals of the dummy load means comprise posts adapted to be received within and mate with the receptacles, and the fastener means comprise set screws mating with threaded holes into the receptacles to be tightened down on the posts, the posts thereby forming said mechanical stop and being dimensioned so that when the set screws are backed away from the posts but retained in the threaded holes for removal of the dummy load means from the connector, the proximal terminals of the electrical lead are insertable fully into the receptacles without interference from the set screws which may then be tightened down on the proximal terminals.

* * * * *